US007148029B2

(12) United States Patent
Brady et al.

(10) Patent No.: US 7,148,029 B2
(45) Date of Patent: Dec. 12, 2006

(54) IMMUNOASSAY FOR NEONICOTINYL INSECTICIDES

(75) Inventors: James Francis Brady, Summerfield, NC (US); Dana Philip Simmons, Summerfield, NC (US); Timothy Edward Wilson, Summerfield, NC (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 704 days.

(21) Appl. No.: 10/149,512

(22) PCT Filed: Dec. 6, 2000

(86) PCT No.: PCT/EP00/12310

§ 371 (c)(1),
(2), (4) Date: Jun. 7, 2002

(87) PCT Pub. No.: WO01/42787

PCT Pub. Date: Jun. 14, 2001

(65) Prior Publication Data

US 2003/0108970 A1 Jun. 12, 2003

Related U.S. Application Data

(63) Continuation-in-part of application No. 09/456,782, filed on Dec. 8, 1999, now abandoned.

(51) Int. Cl.

| | |
|---|---|
| ***G01N 33/535*** | (2006.01) |
| ***C12N 9/96*** | (2006.01) |
| ***C07K 17/06*** | (2006.01) |
| ***C07K 16/44*** | (2006.01) |
| ***C07D 401/08*** | (2006.01) |
| ***C07D 413/06*** | (2006.01) |

(52) U.S. Cl. ..................... 435/7.93; 435/188; 530/404; 530/405; 530/406; 530/388.9; 530/389.8; 546/274.7; 544/68

(58) Field of Classification Search ............. 530/388.9, 530/389.8, 404, 405, 406; 435/7.93, 188; 546/274.7; 544/68
See application file for complete search history.

(56) References Cited

U.S. PATENT DOCUMENTS

| | | | |
|---|---|---|---|
| 5,334,528 | A | 8/1994 | Stanker et al. |
| 5,723,306 | A | 3/1998 | Pullen et al. |

FOREIGN PATENT DOCUMENTS

| | | |
|---|---|---|
| EP | 692127 | 4/1994 |
| JP | 0580553 | 1/1994 |
| JP | 2000191698 | 7/2000 |

OTHER PUBLICATIONS

Li, Kai et al.: "Development of an Enzyme-Linked Immunosorbent Assay for the Insecticide Imidacloprid", J. Agric. Food Chem. (2000), 48(8), 3378-3382.

*Primary Examiner*—Mary E. Ceperley
(74) *Attorney, Agent, or Firm*—Jacqueline Haley

(57) ABSTRACT

The present invention provides immunogens for generating anti-neonicotinoid antibodies as well as antibodies, methods, reagents and kits for determining the presence of one or more neonicotinoid insecticides in a sample by immunoassay. The present invention has particular application to determination of the concentration of neonicotinoid insecticides applied to a plant propagation materials such as seed.

22 Claims, No Drawings

IMMUNOASSAY FOR NEONICOTINYL INSECTICIDES

This application is a 371 of PCT/EP00/12310, filed on Dec. 6, 2000, which is a continuation of U.S. Ser. No. 09/456,782, filed on Dec. 8,1999 now abandoned.

This invention relates to immunoassays for pesticides and to antibodies and reagents for carrying out such assays. The invention further relates to methods of carrying out such assays and to kits comprising reagents to practice such methods. The invention has particular application to the detection and quantitation of neonicotinoid insecticides in a sample.

Insecticides

The use of synthetic insecticides to control insect pests in crops is a universal practice. This practice has gained a high degree of commercial success because it has been shown that such control can increase crop yield. However, effective use of insecticides requires sound management in view of insect resistance and environmental and worker exposure concerns. One solution applied to this problem has been the provision of new, more highly active insecticides in order to reduce the need for older acutely toxic insecticides and to reduce environmental loading rates.

One new class of insecticides that is gaining significant recognition in the market place are the so-called "neonicotinoid" insecticides. Compounds of this class include, for example, the compounds imidacloprid, acetamiprid, and thiamethoxam that are described in U.S. Pat. Nos. 4,742,060 and 5,304,566 and EP580553A2, respectively.

Direct treatment of plant propagation materials (such as seeds) with insecticides are target applications which address the need for a reduction of environmental and worker exposure and pest resistance buildup when applied alone or in conjunction with foliar or furrow insecticide applications. However, care must be taken to ensure that the seed coating apparatus is properly calibrated in order that the insecticide is uniformly applied to the seed material to avoid problems with insecticide performance and seed phytotoxicity, among others. Analytical measurements can be used to determine if the seed coating equipment has been calibrated properly, is operating properly and if treated lots of seed may be released for shipment. However, traditional methods for detecting insecticide residues on seeds are extremely time-consuming and costly, since they require highly specialized and expensive analytical procedures such as gas-liquid or high-performance liquid chromatography. Both chromatographic techniques require expensive instrumentation that is costly to maintain and which must be operated by highly skilled technicians. Seed treatment facilities and growers usually do not have such equipment or personnel on staff so seed samples must be shipped to off-site analytical laboratories. When samples are analyzed on a rapid turnaround basis by such laboratories, the treatment facility may receive analytical data approximately twenty-four hours subsequent to shipment. Less rapid analyses result in more lengthy delays. These delays result in many hours of idle machine time at the coating facility. Delays in shipment of coated seed are also incurred.

There is an urgent need in the art to improve existing measurement techniques to make them less expensive, more efficient and more easily manageable. The desired methods should also be useful outside the laboratory under field conditions, such that they can quickly and reliably provide a grower or seed treatment personnel with information on the presence and concentrations of a given insecticide on a seed sample. In this regard, it is important that the methods differentiate the active pesticidal material from other products allowing quantitative determination of the desired active ingredient present on the seed. However, a number of serious limitations of classical analytical methods still remain. Some of these limitations would be overcome by the use of immunoassay technology.

Immunoassays and Detection of Pesticides

While developed primarily for medical and veterinary use, immunoassays have begun to find more applications in the agricultural arena. For example, immunoassays are available for the detection and quantitation of crop diseases, aflatoxins and certain antibiotics. While immunoassays for pesticide detection have been described in the scientific literature (see below), they have become available on a commercial basis only within the past decade.

Immunoassays rely on highly specific antibody reagents and relatively simple analytical apparatus to detect and/or quantify a wide variety of target materials. The antibody, rather than the instrument or operating conditions, provides the analytical specificity. Immunoassays can therefore be performed on relatively crude samples. Furthermore, immunoassay methods have been optimized for use in remote, non-laboratory settings, allowing their use in the field as well as in the specialized laboratory.

Immunological methods are known for the detection of certain herbicides, including 2,4-dichlorophenoxyacetic acid (Fleeker, J., *J. Assoc. Off. Anal. Chem.* 70:874–878 (1986)), chlorsulfuron (Kelley, M. et al., *J. Agric. Food Chem.* 33:962–965 (1985)), haloacetamides (Winzenburger, P. A. et al. (European Patent Publication EP 340198, 1989), and a variety of pesticides, including diflubenzuron (Wie, S. I. et al., *J. Agric. Food Chem.* 30:949–957 (1982)), metalaxyl (Newsome, W. H., *J. Agric. Food Chem.* 33:528–530 (1985)) and parathion (Ercegovich, C. D. et al., *J. Agric. Food Chem.* 29:559–563 (1981)). A method has also been described for the immunologic detection of atrazine (U.S. Pat. No. 4,530,786). Immunological assays for cyanazine, diclofop-methyl, phentachlorphenol, 2,4,5-T and terbutryn are also known.

All of the above immunological methods utilized polyclonal antisera that were obtained from host animals (typically rabbits) immunized with an appropriate antigen (immunogen). More recently, monoclonal antibodies (mAbs) specific for atrazine and its derivatives and breakdown products, and use of such mAbs in immunoassays, have been disclosed (Schlaeppi et al., European Patent Publication EP 365818 (1990)).

Because of their low molecular weight, insecticides are not immunogenic and do not elicit specific antibodies from animal hosts. Hence, development of an insecticide immunoassay requires a number of steps, beginning with the design of haptens, derivatives of the insecticide that maintain the structural specificity of the insecticide molecule while permitting conjugation to a higher molecular weight immunogenic "carrier" protein. Furthermore, for screening antibodies during the process of their production, additional haptens may also be prepared whose chemical structures vary from the hapten used to immunize animals. Finally, once an antibody preparation is obtained (either polyclonal or monoclonal), a sufficiently sensitive immunoassay must be developed.

Basic strategies used in modern immunoassays have been described in numerous references (See, for example, Voller, A. et al., eds., *Immunoassays For The 80's*, University Park, 1981; Voller, A., "The Enzyme Linked Immunosorbent Assay (ELISA)", *Diagnostic* Horizons 2:1–7, 1978, Microbiological Associates Quarterly Publication, Walkersville, Md.; Voller, A. et al., *J. Clin. Pathol.* 31:507–520 (1978); Butler, J. E., *Meth. Enzymol.* 73:482–523 (1981); Maggio, E. (ed.), *Enzyme Immunoassay*, CRC Press, Boca Raton, Fla., 1980). Essential to each approach is the generation of calibration curves using known amounts of the desired analyte.

A "labeled antibody" method in common use is referred as the enzyme-linked immunosorbent assay (ELISA). Here, a protein conjugate of the pesticide (called a "coating" or "screening antigen") is prepared using a protein that is structurally unrelated to the carrier protein used in the pesticide immunogen, against which the anti-pesticide antibodies were generated. The coating antigen conjugate is immobilized on a solid phase support, such as the surface of a microplate well, resulting in a fixed amount of solid phase pesticide per reaction. A known amount of antibody is added along with the test sample. The immobilized pesticide competes with the free pesticide in the unknown sample for a limited number of antibody binding sites. The interaction between antibody and analyte in the liquid phase inhibits the binding of antibody to the solid phase pesticide. Antibody bound to the solid phase is detected by an enzyme-conjugated second antibody specific for the constant region of the heavy chain of the anti-pesticide antibody. Many enzyme-linked second antibodies are commercially available for such use. After washing away unbound second antibody, immobilized second antibody is typically detected by adding a chromogenic substrate for the enzyme, which results in a colored reaction product formed in direct proportion to the amount of second antibody bound. The amount of reaction product is thus inversely proportional to the amount of analyte in the unknown sample.

A modification of the "labeled antibody" method eliminates the use of coating antigen. The enzyme immunoassay (EIA) immobilizes the anti-pesticide antibody on a solid phase. A pesticidal hapten is covalently coupled to an enzyme, and the resulting enzyme conjugate is incubated with samples in microwells or culture tubes coated with anti-pesticide antibody. Pesticide in the sample competes with the pesticidal hapten-enzyme conjugate to bind to immobilized antibody. The solid phase is washed to remove unbound materials and antibody-bound enzyme conjugate is detected by addition of chromogenic substrate. See, e.g., Bushway, R. J., L. P. Perkins, S. A. Savage, S. L. Lekousi, and B. S. Ferguson. 1988. Determination of atrazine residues in water and soil by enzyme immunoassay. Bull. Environ. Contam. Toxicol. 40:647–654; Fleeker, J. R. and L. W. Cook. 1991. Reliability of commercial enzyme immunoassay in detection of atrazine in water. P. 78–85 in M. Vanderlann, L. H. Stanker, B. E. Watkins, and D. W. Roberts., eds. Immunoassays for Trace Chemical Analysis. ACS Symposium Series 451. Washington, D.C.: American Chemical Society.

There is a need in the agricultural field for a method of analyzing seeds treated with active ingredients such as insecticides that can be carried out in the field or within a seed treatment facility.

The present invention provides neonicotinoid haptens and immunogens for generating anti-neonicotinoid antibodies as well as antibodies, methods, reagents, and kits for determining the presence of one or more neonicotinoid insecticides in a sample by immunoassay. The present invention has particular application to determination of the concentration of neonicotinoid insecticides applied to plant propagation materials such as seed.

The immunoassay method of the invention enables personnel at seed treatment facilities where neonicotinoid insecticides are applied to seeds to quantitatively measure the amount of active ingredient applied. The method involves a rapid extraction of the active ingredients from the seed and rapid immunoassay-based measurement of the extract solution. These measurements can be used to determine if the seed coating equipment has been calibrated properly, is operating properly, and if treated lots of seed may be released for shipment. The assay is designed to be simple to operate requiring only ordinary laboratory equipment and reagents. Therefore, personnel lacking expertise in performing immunoassays will be able to successfully conduct the test after a few practice trials.

It has been found that antigenic neonicotinoid conjugates (immunogens) can be made by conjugation of a neonicotinoid pesticidal hapten to a carrier molecule such as purified protein derivative (PPD, Tuberculin) from Diptheria virus, bovine serum albumin, human serum albumin, ovalbumin or keyhole limpet hemocyanin to a neonicotinoid hapten. Conjugates of derivatized materials such as derivitized bovine serum albumin, cationized bovine serum albumin and the like also can be made. See A. Muckerheide, R. Apple, A. Pesce and J. G. Michael (1987) J. Immunol. 138:833–837. These immunogens can then be injected into host animals that will produce antibodies to the neonicotinoid hapten which may be harvested. These antibodies may then be utilized in a variety of immunoassay procedures to detect corresponding neonicotinoid insecticides, using various known markers to label either the insecticide or antibody. In some embodiments of immunoassays, either a neonicotinoid insecticide derivative or an antibody is immobilized. Both polyclonal and monoclonal antibodies can be used in the practice of the present invention. The antibodies can be shown to selectively bind to the desired neonicotinoid insecticide(s) even in the presence of other pesticidal active ingredients including other neonicotinoid insecticides incorporated in a seed coating formulation.

Detection methods that can be applied to the practice of the present invention for measurement of neonicotinoid insecticides in a sample include biosensors and enzymatic, fluorescent, chemiluminescent and radioimetric systems. Such assays may use heterogeneous or homogeneous formats and may use microwell plates, culture tubes, and latex beads or particles as solid phases.

The immunoassays of the present invention are used to determine the concentration of neonicotinoid insecticide compounds such as imidacloprid, nitenpyram, acetamiprid, thiamethoxam, thiacloprid and clothiadin in a sample such as a plant propagation material.

The present invention provides immunoassays for testing a sample for the presence of neonicotinoid insecticides. In such immunoassays, the neonicotinoid (antigen)/antibody reaction can be detected by a variety of methods, using various markers to label either the antigen or antibody to permit detection of the reaction product. Furthermore, immobilization of either the antigen or antibody will facilitate detection in many cases.

Antigen/antibody assays can be generally classed into two categories, heterogeneous and homogeneous. Heterogeneous assays require separation of the bound-labeled component from the free-labeled component prior to detection of the reaction product. Homogeneous assays do not require such a separation step. The assays can further be (1) competitive, for example, where antigen competes for labeled antibody with a solid-phase antigen or where antigen competes with labeled antigen for a solid-phase antibody or (2)

noncompetitive where there is a direct relationship between label and antibody or antigen.

Immunoassay methods that can be used in the practice of the present invention to detect neonicotinoid insecticides in a sample include enzyme, fluorescent chemiluminescent and biosensor immunoassay, as well as radioimmunoassay. In an enzyme-linked immunoassays (ELISA), in accordance with the present invention, haptens corresponding to the neonicotinoid insecticide(s) of interest can be labeled directly with an enzyme or indirectly by use of enzyme-labeled antibodies which under appropriate conditions catalyze a reaction with a substrate. The enzyme activity is typically detected by formation of a colored reaction product i.e., a colored end point that may be easily detected by eye or measured by spectroscopic or reflectance means.

In fluorescent immunoassay techniques for use in the present invention, haptens corresponding to the neonicotinoid insecticide(s) of interest can be labeled directly with fluorochromes, or indirectly with fluorochrome-labelled antibodies. Fluorochromes are dyes that absorb radiation (e.g., ultraviolet light), are excited by it, and emit light (e.g., visible light).

In one embodiment of the present invention, the method for determining the concentration of a neonicotinoid insecticide in a sample comprises the steps of:

(a) providing a solid phase with an immobilized antibody selective for said neonicotinoid insecticide;
(b) contacting said sample with the immobilized antibody in the presence of a known amount of a neonicotinoid insecticide hapten-enzyme conjugate;
(c) washing the solid phase of step (b) to remove any unbound hapten-enzyme conjugate or sample;
(d) reacting a chromogenic substrate specific for said hapten-enzyme conjugate with the washed solid phase of step (c) in order to generate a chromogen; and
(e) measuring the amount of the chromogen produced by step (d) in order to determine the amount of antibody-bound hapten-enzyme conjugate and hence the amount of neonicotinoid insecticide in said sample.

In one embodiment, the immunoassay is supplied in the form of a kit including antibody-coated tubes, the neonicotinoid hapten-enzyme conjugate, enzyme substrate, and solution to terminate production of the colorimetric signal.

While the invention often is described with reference to the use of polyclonal antibodies, those skilled in the art will also recognize that monoclonal antibodies could be used as an alternative to using polyclonal antibodies. The term "antibodies" is used herein to generically refer to polyclonal or monoclonal antibodies.

Monoclonal antibodies to neonicotinoid insecticides for use in the practice of the present invention are made using immunization and hybridoma culturing techniques well known to those in the art. Suitable hybridoma cell lines are preferably produced by the fusion of an antibody producing cell and a myeloma cell derived from a murine species. The antibody producing cells are preferably spleen cells. Any suitable myeloma cell line may be used however it is desirable to use a well characterized cell line of which a number are in common usage.

Likewise, polyclonal antibodies to neoticotinoid insecticides for use in the practice of the present invention are also made using techniques known to those skilled in the art.

The present invention also provides a polyclonal IgG antibody preparation which binds at least one neonicotinoid insecticide, the antibody preparation produced by a method which comprises the steps of: (a) administering to a host a predetermined quantity of a composition comprising a neonicotinoid insecticide or an immunological equivalent coupled to a biologically acceptable carrier protein, (b) collecting sera from the host, and (c) purifying IgG antibody from the sera. An immunological equivalent of an antigen has the ability, when introduced into a host, to cause the production of antibodies to the antigen.

As noted above, the immunoassay of the present invention has particular application in detecting the amount of a neonicotinoid insecticide that has been applied to a plant propagation material. The term "plant propagation material" is understood to denote all the generative parts of the plant such as seeds which can be used for the multiplication of the latter and vegetative plant material such as cuttings and tubers (for example potatoes). There may be mentioned, e.g., the seeds (in the strict sense), roots, fruits, tubers, bulbs, rhizomes, and parts of plants. Germinated plants and young plants which are to be transplanted after germination or after emergence from the soil, may also be mentioned. These young plants may be protected before transplantation by a total or partial treatment by immersion.

In one embodiment, the neonicotinoid insecticide detectable by the assay of the present invention is represented by the formula (I)

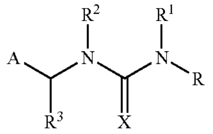

wherein A is 2-chloropyrid-5-yl or 2-chlorothiazol-5-yl;

R and $R^3$ independently are hydrogen or $C_1$–$C_4$alkyl;

$R^1$ are $R^2$ independently are hydrogen or $C_1$–$C_4$alkyl or $R^1$ and $R^2$ are taken together with the nitrogen atoms to which they are attached to form an imidazolidine or an oxadiazine ring; and X is N—$NO_2$ or N—CN.

In another embodiment, the neonicotinoid insecticide detectable by the assay of the present invention is represented by the formula (III)

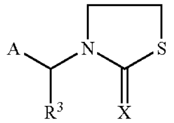

wherein A, $R^3$ and X are as defined above for formula (I).

In a preferred embodiment, the immunoassay of the present invention employs polyclonal antibodies for a neonicotinoid insecticide. These antibodies can be obtained from the sera of an immunized animal. Immunization can be accomplished by injecting the immunogen (hapten-PPD antigenic conjugate) into an antibody producing species, typically a mammal and preferably a rabbit or sheep. Typically, an initial injection is followed by a series of subsequent booster injections to maximize the antibody response. Optimally, the injection regime is in multiple doses given to female New Zealand white rabbits. The amount of immunogen injected varies but must be adequate to elicit a detectable amount of antibody. Antibody production can be verified by analyzing sera obtained in trial bleeds using EIA, ELISA or Indirect Fluorescent Immunoassay Assay.

The same labels used in known immunometric assays can be used to label the hapten used in the present invention. Among these may be mentioned reporter molecules (RM) including enzymes, such as alkaline phosphatase, horseradish peroxidase, and β-galactosidase. In addition, fluorescent, luminescent or radioactive labels such as fluorescein, rhodamine, luminol, acridium and radioactive isotopes $^{125}I$, etc., or colloidal particles such as gold and selenium, etc., can be used. Finally, lanthanide chelate flourophores such as europium and terbium may be used to generate time-resolved fluorescent signals. The most common enzymatic markers are horseradish peroxidase (HRP) and alkaline phosphatase.

In one embodiment, a spectrophotometer is used to detect the amount of neonicotinoid in a sample. However, the methods of the present invention can be adapted by one skilled in the art to use in other types of chromogenic detectors. Similarly, the detectable reaction product is not limited to a chromophore but includes other labels as described above.

Haptens of the following formulae (IA), (IB) and (IIA) have been found to be useful in producing antigenic neonicotinoid conjugates (immunogens) and assay conjugates:

Hapten (IA)

(IA)

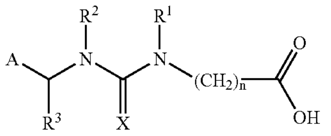

wherein A is 2-chloropyrid-5-yl or 2-chlorothiazol-5-yl;

$R^3$ is hydrogen or $C_1$–$C_4$alkyl;

$R^1$ and $R^2$ independently are hydrogen or $C_1$–$C_4$alkyl or $R^1$ and $R^2$ are taken together with the nitrogen atoms to which they are attached to form an imidazolidine or an oxadiazine ring;

n is an integer from 1 to 5 (preferably an integer from 3 to 5); and

X is O, N—$NO_2$ or N—CN.

Hapten (IB)

(IB)

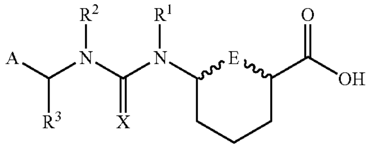

wherein A, $R^1$, $R^2$, $R^3$ and X are as defined in formula (IA); and

E is a single covalent bond or is a linking moiety of the formula —$(CH_2)_m$— wherein m is an integer from 1 to 3.

Example 1

Hapten (IIIA)

(IIIA)

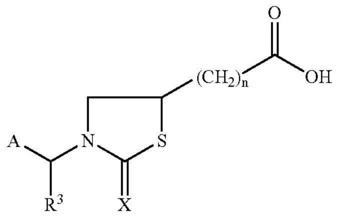

wherein A, $R^3$, X and n are as defined for formula (IA).

Hapten (IIIB)

(IIIB)

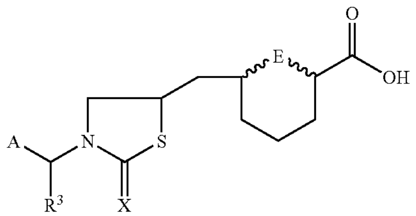

wherein A, $R^3$ and X are as defined for formula (IA) and E is as defined for formula (IB).

Haptens of formulae (IIIA) and (IIIB) can be prepared in analogy to the following methodology:

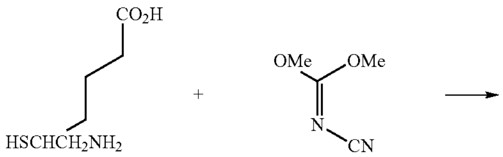

2-aminoethanethiol denvative (N-cyanoimido)carbonate

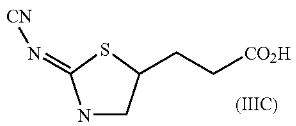

(IIIC)

Substituted 2-(N-cyanoimino) thiazolidine

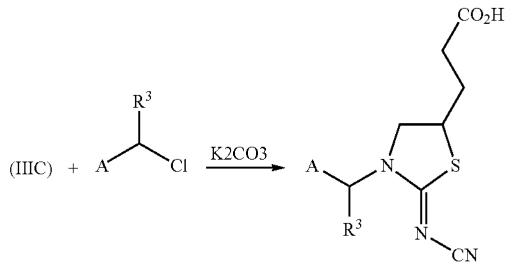

The desired hapten (IIIA) or (IIIB) is prepared by using an appropriate 2-aminoethanethiol derivative selected from a compound of the formulae:

(IIID)

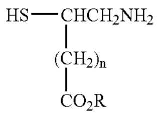

or (IIIE)

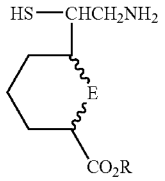

wherein R has the meaning given above for formula (I).

The following haptens have been found to be particularly useful in the practice of the present invention:

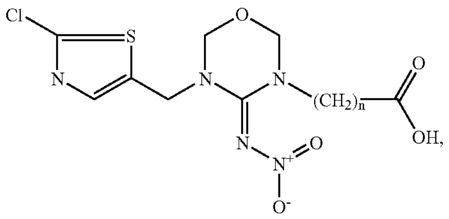

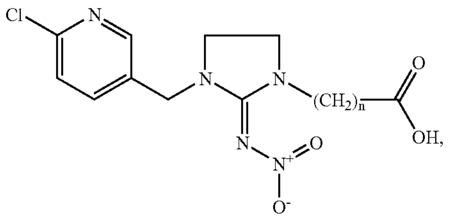

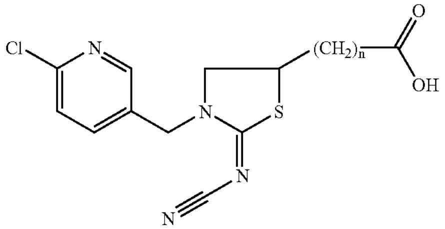

and

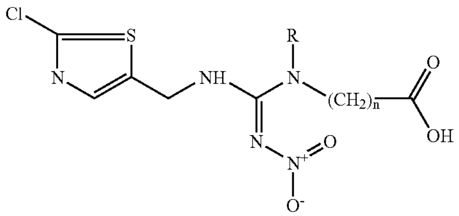

wherein n in each case is an integer from 1 to 5; preferably n is an integer from 3 to 5.

Antigenic neonicotinoid conjugates (immunogens) and assay conjugates can be made by conjugation of a neonicotinoid pesticidal hapten to a carrier molecule or reporter moleclue, as the case may be, using techniques known to those skilled in the art. Two basic approaches have been taken. The first uses linkers which become part of the conjugate. These linkers are homobifunctional or heterobifunctional, and include those capable of forming, for example, disulfide linkages through the thiol groups of cysteine moieties in the substrate proteins, or of the formation of amide linkages between N-terminal amino group or the amino side chains or lysine residues and activated acyl moieties such as succinimidyl esters. In general, this approach involves highly reactive functional groups on the linker and is reasonably facile with respect to the substrates for conjugation. However it is often useful to employ functional groups which may be less reactive, such as those capable of hydrazone formation.

A second approach, particularly useful in conjugating two protein moieties, uses a dehydrating agent such as a carbodiimide to effect the formation of, for example, new peptide bonds by reaction of a carboxyl moiety on one member of the conjugate with a free amino group on the other. In this case, the reagent does not become part of the conjugate.

This reaction is not particularly facile since the carboxyl group is not activated; the carbodiimide provides the active intermediate and shifts the equilibrium by removing the elements of water to form the peptide bond.

Both approaches to conjugation have generally been conducted in aqueous solvents because the protein material forming the conjugate is easily denatured. Proteins are designed to be stable in an aqueous environment and are known to denature even in solvents, such as ethanol, which would be thought to be reasonably analogous to an aqueous medium. Also, protein conjugate components tend to be relatively insoluble in nonaqueous solvents.

Hapten conjugates of the following formula have been found to be useful in the practice of the invention:

(II)

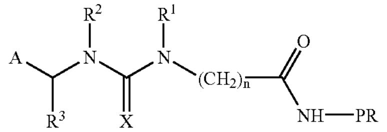

wherein A, $R_1$, $R_2$, $R_3$, n and X have the meanings given in formula (IA) above and PR is a protein residue of: (1) a carrier molecule such as a purified protein derivative (PPD, Tuberculin) from Diptheria virus, bovine serum albumin, human serum albumin, ovalbumin or keyhole limpet hemocyanin in the case of an immunogen or (2) a reporter molecule (RM) such as alkaline phosphatase, horseradish peroxidase, and β-galactosidase.

In addition, hapten conjugates of the following formula are similarly useful:

(IIA)

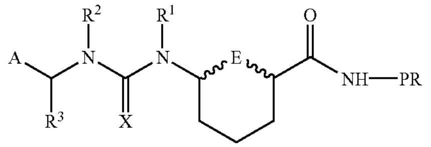

wherein A, $R_1$, $R_2$, $R_3$, E and X have the meanings given in formula (IB) above.

The following conjugates have been found to be particularly useful in the practice of the present invention:

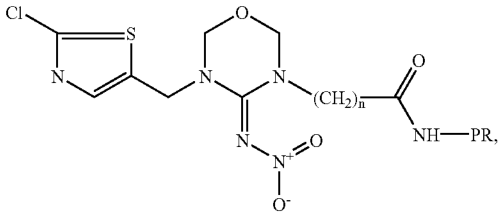

,

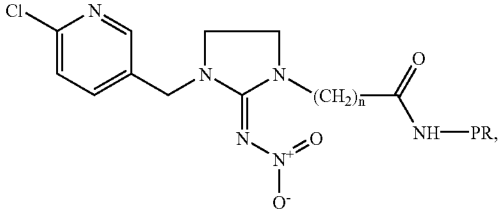

,

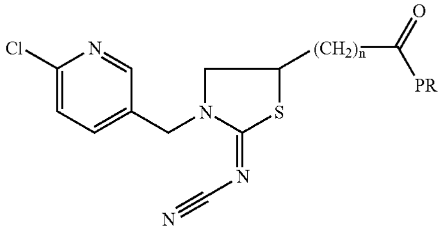

and

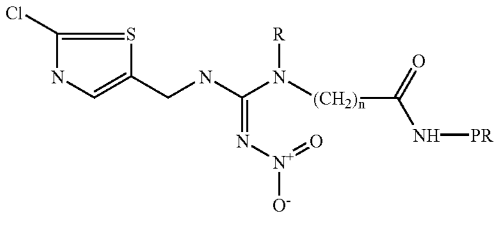

wherein n in each case is an integer from 1 to 5; preferably n is an integer from 3 to 5.

The unlabeled polyclonal antibody used in the process of the present invention to bind the antigenic neonicotinoid or hapten-RM conjugate in the sample being tested can be immobilized on any of the supports commonly used in immunometric assays. Among those that may be used are filter paper, latex or polystryene beads and polyethylene, polystyrene, polypropylene or other suitable microwell plate or test tube. This support can be made of any polymer of natural or synthetic origin, or of an amorphous material such as glass. Advantageously, membranes of nitrocellulose or nylon are used for the reactive strips, and polyvinyl, polypropylene, polystyrene or other plastics for the beads or microplates. Gels or particles based on agarose, acrylamide or latex can also be used. Additionally, any of the immunochromatographic devices, test strips and lateral flow devices known in the art can be adapted to the process of the present invention. Among the suitable lateral flow devices, there can be mentioned, for example, the type of lateral flow device disclosed in U.S. Pat. No. 4,366,241. The techniques for bonding antibodies to such materials are well known to those skilled in the art. A suitable source for obtaining antibodies bound to a support is, for example, Beacon Analytical Systems, Inc. (Portland, Me.).

To prepare a seed sample for use in the assay, representative subsamples of seed from a neonicotinoid treated lot (for example, from five to 100 grams of canola seed; from ten to 200 grams of sorghum, wheat, cotton, field corn or sweet corn seed) are dispersed in a suitable solvent such as acetone, acetontrile, ethanol, isopropanol, methanol, or mixtures of these solvents with various percentages of water. Suitable solvent-water mixtures include, for example, from 1 to 50% $MeOH/H_2O$ and from 1 to 20% acetonitrile/$H_2O$. The dispersed seed is mixed by vortexing and then placed in a sonicating bath for about twenty minutes and followed by additional vortexing. The contents are allowed to settle. A known portion of the liquid extract is removed and added to known quantity of a solution of, for example, 1% acetonitrile/water. The extract is diluted further to bring the concentration of the extracted neonicotinoid into the range of the calibration curve. Dilutions of one thousand- to sixty thousand-fold have been found to be useful. The immunoassay takes approximately thirty-five minutes to run. The extraction and preparation of the extract for analysis takes approximately thirty minutes. Therefore, a seed sample can be extracted and analyzed in approximately one hour and five minutes. In one embodiment, up to two seed samples (with up to five subsamples per seed sample) can be analyzed at one time.

Concentrations of neonicotinoid insecticides from about ten thousand parts per million to one-half part per billion can be detected in the immunoassays according to the present invention. However, the method is suitable for any amount of neonicotinoid insecticide present as long as the amount of neonicotinoid insecticide in a sample or sample extract falls or may be appropriately diluted to fall within the range of the calibration curve.

The preparation of the antigen, production of the polyclonal antibodies and an immunoassay are illustrated in more detail by the following non-limiting examples.

EXAMPLES

Example 1

Synthetic Procedure for Thiamethoxam Hapten

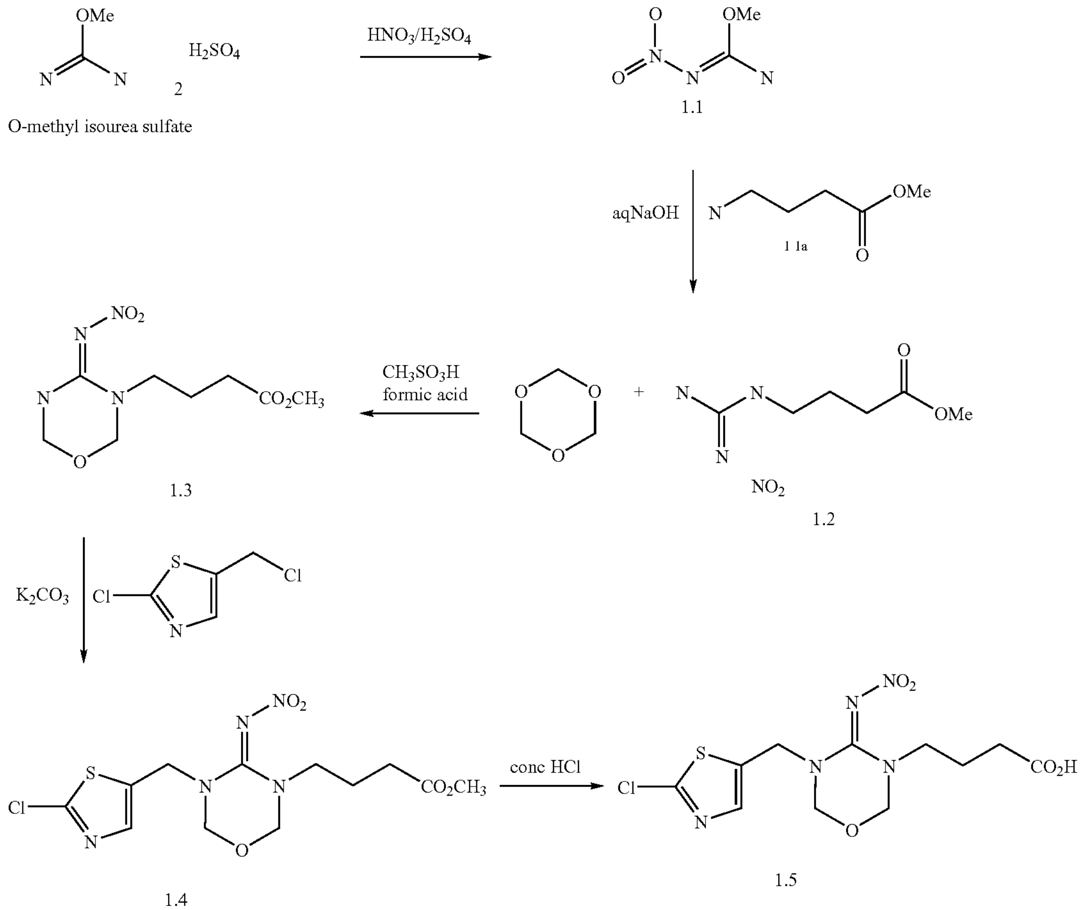

O-methyl isourea sulfate
1.1
1 1a
1.2
1.3
1.4
1.5

1.1 2-methyl-1-nitroisourea

Dissolve O-methyl isourea sulfate (38.5 g) in a nitric acid (120 ml)/sulfuric acid (280 ml) mixture at 0° C. and stir for 2 h at 0° C. Carefully pour the mixture onto crushed ice with stirring and then remove the crushed ice by filtration. Dissolve the needle-like crystals d in ethyl acetate and make the solution alkaline by addition of potassium carbonate. Dry the solution over magnesium sulfate and filter. Concentrate the filtrate to yield a white powder (5 g).

1.2

A solution is prepared from 3 g of methyl 4-aminobutyrate hydrochloride (1.1a) and 15 ml of water. The pH is adjusted to 11 by dropwise addition of 2N NaOH while the solution is cooled in an ice bath. The reaction flask is equipped with a pH electrode and thermometer and the resultant clear basic solution is stirred rapidly as 2-methyl-1-nitroisourea (2.38 g) is added in small portions to maintain the temperature of the solution below 2° C. When the addition is complete, stir the reaction for 1.5 h at 0° C.; note the pH has stabilized at 9.6. Add THF (1 ml) and stir for an additional 2 h. Dilute the reaction with water and pour on to ethyl acetate. After the organic phase separates, dry the organic fraction over magnesium sulfate and filter the solution. Concentrate the filtrate to yield a clear oil. Flash chromatograph the crude oil on silica gel eluting with 3:1 dichloromethane/acetonitrile to afford 750 mg of the desired product as a white solid.

1.3

Combine the product from 1.2 (1.44 g) with paraformaldehyde (422 mg), methane sulfonic acid (0.023 ml), and formic acid (10 ml) and heat at 55° C. for 15 h. Concentrate the reaction in vacuo. Suspend the resultant brown oil in toluene and azeotropically strip the solution to dryness. Dissolve the resulting oil in 1:1:1 THF/dioxane/acetonitrile and treat it with excess diazomethane. Stir this solution for 30 min and treat the reaction with acetic acid. Concentrate the reaction mixture to an oil. Reconstitute the oil in ethyl acetate, wash with dilute sodium bicarbonate solution, dry over magnesium sulfate, and re-concentrate to an oil. Purify this oil by flash chromatography in 3:1 dichloromethane/acetonitrile to provide 658 mg of the desired oxadiazinamine butyric ester (1.3) as a clear oil.

1.4

Dissolve the product from 1.3 (1.1 g) d in acetonitrile (50-ml) and add 3 g of potassium carbonate. Add the chloromethyl chlorothiazole in one portion and heat the reaction mixture at 55° C. for 20 h. Cool the reaction mixture to room temperature and filter to remove solids. Concentrate the resultant brown filtrate to an oil. Purify the oil by flash chromatography in 3:1 dichloromethane/acetonitrile to afford 894 mg of the desired compound as a yellow/brown oil.

1.5

Dissolve compound 1.4 (372 mg) in 8-ml of conc. HCL and 1 ml of water and stir for 6 h at room temperature. Dilute the reaction mixture with water and carefully basify by addition of 1 N NaOH until a pH of 4.5 is attained. Extract with ethyl acetate and dry the organic fraction over magnesium sulfate. Concentrate the dried organic fraction to an oil and purify by flash chromatography in 1:1 dichloromethane/acetonitrile to afford the desired product 1.5 (100 mg).

(1.5)

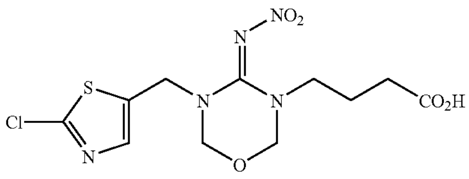

Examples 2–5

Thiamethoxam Haptens

The synthetic methodology of Example 1 is used to prepare the following thiamethoxam haptens shown in Table 1 by replacing the intermediate 1.1a with an appropriate analog compound of the formula $NH_2(CH_2)_nCO_2R$ (1.1 b) wherein n is an integer from 1 to 5 and R is H or $C_1$–$C_4$alkyl.

TABLE 1

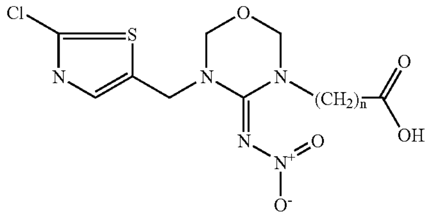

| Example | n |
|---|---|
| 2 | 1 |
| 3 | 2 |
| 4 | 4 |
| 5 | 5 |

Examples 6–9

Thiamethoxam Haptens

The synthetic methodology of Example 1 is used to prepare the following thiamethoxam haptens shown in Table 2 by replacing the intermediate 1.1a with an appropriate analog compound of the formula (1.1c)

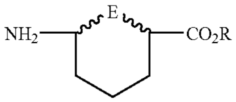

(1.1c) where E is a covalent single bond or a linking moiety $-(CH_2)_m-$ wherein m is an integer of 1 to 3; R is H or $C_1$–$C_4$alkyl.

TABLE 2

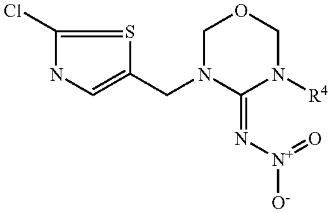

| Example | $R^4$ |
|---|---|
| 6 | 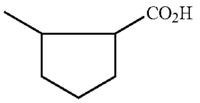 |
| 7 | 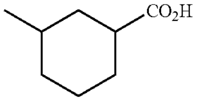 |
| 8 | 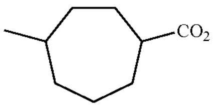 |
| 9 | 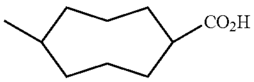 |

Example 10

Synthetic Procedure for Des-nitroimino Thiamethoxam Hapten

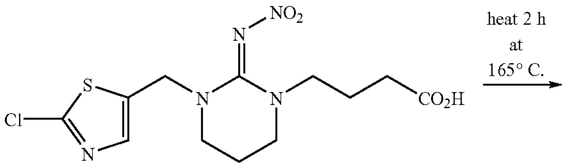

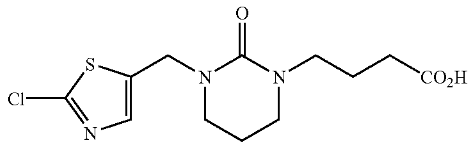

Procedure:

Thiamethoxam-butyric acid hapten (100 mg, 0.275 mmol) and anisole (6.5 ml) were combined in a 10 ml round-bottomed flask equipped with a magnetic stir bar and a reflux condenser. The flask was placed in an oil bath and heated at 165° C. for 2 h. The anisole was removed under reduced pressure at 50° C. for 5 h. The resulting oily product (90.2 mg) was 93% pure by HPLC analysis.

Spectroscopic Data for Characterization:

HPLC: Keystone Scientific Aquasil C-18 5u (25×0.46 cm); Acetonitrile: 20 mM Phosphoric Acid (40:60); 1.0 ml/min.; T=40C; UV @ 240 nm (BW=100 nm); Run Time: 13 min.; Retention Time: 4.6 min.

TLC: (diol gel) Dichloromethane/Acetonitrile, 2:1 Rf=0.25.

$^1$H NMR ($CD_3CN$, 300 MHz): δ 7.43 (t, 1H), 4.78 (s, 4H), 4.75 (s, 4H), 4.48 (d, 2H), 3.29 (t, 2H), 2.27 (t, 2H), 1.73 (q, 2H).

EI/DEP Mass Spectrum: m/z 319 (M+).

Combustion Analysis: Theoretical: C, 41.32; H, 4.41; N, 13.14;

Found: C, 40.13; H, 4.43; N, 12.99

Examples 11–18

Des-nitroimino Thiamethoxam Haptens

The synthetic methodology of Example 10 is used to prepare the following des-nitroimino thiamethoxam haptens shown in Table 3 by replacing the compound obtained in example 1 with an appropriate analog compound of examples 2–9.

TABLE 3

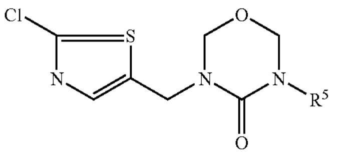

| Example | $R^5$ |
|---|---|
| 11 | $—CH_2CO_2H$ |
| 12 | $—CH_2CH_2CO_2H$ |
| 13 | $—CH_2CH_2CH_2CH_2CO_2H$ |
| 14 | $—CH_2CH_2CH_2CH_2CH_2CO_2H$ |
| 15 | 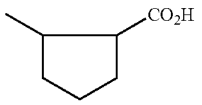 |
| 16 | 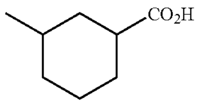 |
| 17 | 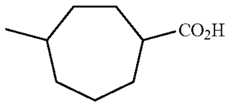 |
| 18 | 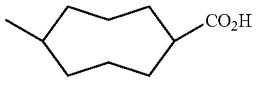 |

Example 19–27

Imidacloprid Haptens

The synthetic methodology of Example 1 is used to prepare the following haptens of imidacloprid shown in Table 4 by use of the nitroguanidyl derivative obtained in 1.2 or an analog thereof obtained by by replacing the intermediate 1.1a with an appropriate analog of formula 1.1b or 1.1c as shown in examples 2–9.

TABLE 4

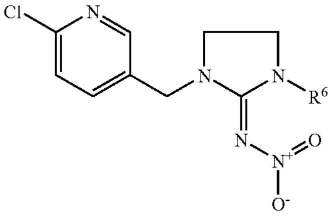

| Example | $R^6$ |
|---|---|
| 19 | $—CH_2CO_2H$ |
| 20 | $—CH_2CH_2CO_2H$ |
| 21 | $—CH_2CH_2CH_2CO_2H$ |
| 22 | $—CH_2CH_2CH_2CH_2CO_2H$ |
| 23 | $—CH_2CH_2CH_2CH_2CH_2CO_2H$ |
| 24 | 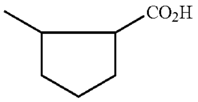 |
| 25 | 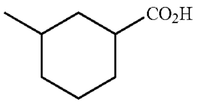 |
| 26 | 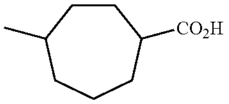 |
| 27 | 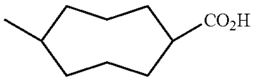 |

Examples 28–36

Des-nitroimino Imidacloprid Haptens

The synthetic methodology of Example 10 is used to prepare the following des-nitroimino imidacloprid haptens shown in Table 5 by replacing the compound obtained in example 1 with an appropriate analog compound of examples 19–27.

TABLE 5

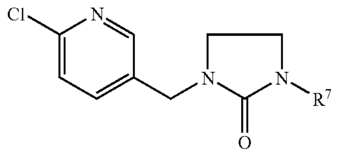

| Example | $R^7$ |
|---|---|
| 28 | $—CH_2CO_2H$ |
| 29 | $—CH_2CH_2CO_2H$ |
| 30 | $—CH_2CH_2CH_2CO_2H$ |
| 31 | $—CH_2CH_2CH_2CH_2CO_2H$ |
| 32 | $—CH_2CH_2CH_2CH_2CH_2CO_2H$ |
| 33 | 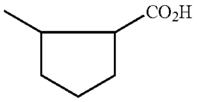 |
| 34 | 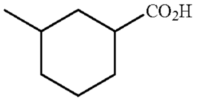 |
| 35 | 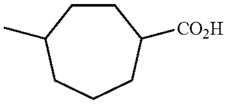 |
| 36 | 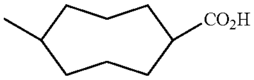 |

Examples 37–45

Clothiadin Haptens

The synthetic methodology of Example 1 is used to prepare the following haptens of clothiadin shown in Table 6 by use of the nitroguanidyl derivative obtained in 1.2 or an analog thereof obtained by by replacing the intermediate 1.1a with an appropriate analog of formula 1.1b or 1.1c as shown in examples 2–9.

TABLE 6

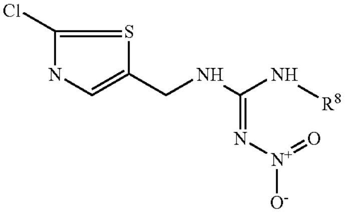

| Example | $R^8$ |
|---|---|
| 37 | $—CH_2CO_2H$ |
| 38 | $—CH_2CH_2CO_2H$ |
| 39 | $—CH_2CH_2CH_2CO_2H$ |
| 40 | $—CH_2CH_2CH_2CH_2CO_2H$ |
| 41 | $—CH_2CH_2CH_2CH_2CH_2CO_2H$ |

TABLE 6-continued

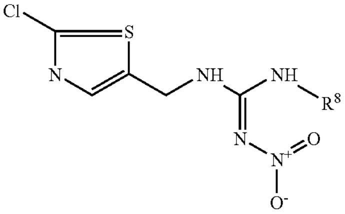

| Example | $R^8$ |
|---|---|
| 42 | 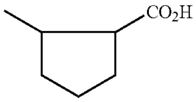 |
| 43 | 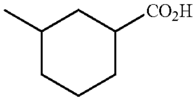 |
| 44 | 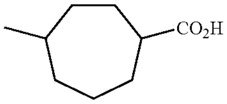 |
| 45 | 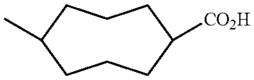 |

Examples 46–54

Des-nitroimino Haptens

The synthetic methodology of Example 10 is used to prepare the following des-nitroimino clothiadin haptens shown in Table 7 by replacing the compound obtained in example 1 with an appropriate analog compound of examples 37–45.

TABLE 7

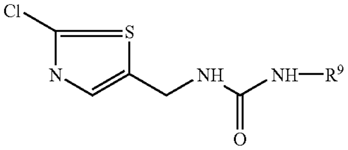

| Example | $R^9$ |
|---|---|
| 46 | $—CH_2CO_2H$ |
| 47 | $—CH_2CH_2CO_2H$ |
| 48 | $—CH_2CH_2CH_2CO_2H$ |
| 49 | $—CH_2CH_2CH_2CH_2CO_2H$ |
| 50 | $—CH_2CH_2CH_2CH_2CH_2CO_2H$ |
| 51 | 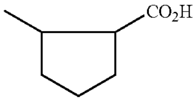 |
| 52 | 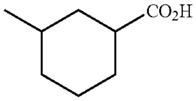 |

TABLE 7-continued

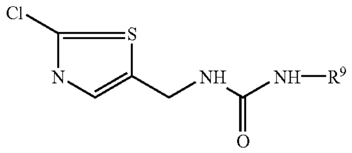

| Example | $R^9$ |
|---|---|
| 53 | 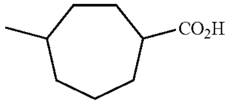 |
| 54 | 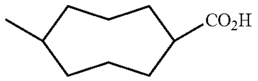 |

Examples 55–63

Thiacloprid Haptens

The synthetic methodology specified for haptens of formulae (IIIA) and (IIIB) is used to prepare the following haptens of clothiadin shown in Table 8.

TABLE 8

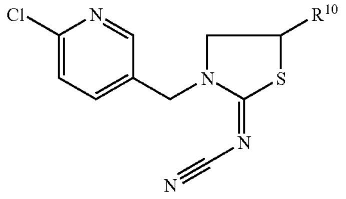

| Example | $R^{10}$ |
|---|---|
| 55 | $—CH_2CO_2H$ |
| 56 | $—CH_2CH_2CO_2H$ |
| 57 | $—CH_2CH_2CH_2CO_2H$ |
| 58 | $—CH_2CH_2CH_2CH_2CO_2H$ |
| 59 | $—CH_2CH_2CH_2CH_2CH_2CO_2H$ |
| 60 | 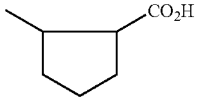 |
| 61 | 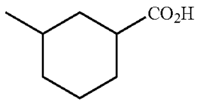 |
| 62 | 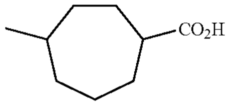 |
| 63 | 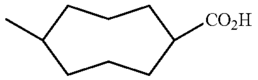 |

Example 64

Preparation of Thiamethoxam Immunogen 64.1

Prepare a solution of the purified protein derivative (Tuberculin, PPD) in 0.01 M PBS, pH 7.4, to a concentration of 1 mg/ml. Adjust the pH of a 0.5 ml aliquot of this solution to 4.5–5.0 with 0.1M HCl.

64.2

Dissolve the thiamethoxam hapten from Example 1 (1 mg) in 250 μl of 0.1 M 2-(N-morpholino)-ethanesulfonic acid, pH 4.5. Combine the hapten and PPD solutions.

64.3

Dissolve 1 mg of 1-(dimethylaminopropyl)-3-ethylcarbodiimide hydrochloride (EDC) in 100 μl of distilled, deionized water. Immediately add the EDC solution to the hapten-PPD solution of 3.2. Mix the hapten-PPD-EDC solution by rotation for 2 hrs at room temperature. Transfer the reaction mixture to a dialysis bag with a 1000–2000 Dalton molecular weight cut-off. Dialyze extensively against 2 liters of PBS at 4° C. with three changes/day for forty-eight hours.

Example 65

Preparation of Imidacloprid Immunogen

The methodology of Example 64 is used to prepare an imidacloprid immunogen using the hapten of Example 21.

Example 66

Preparation of Clothiadin Immunogen

The methodology of Example 64 is used to prepare a clothiadin immunogen using the hapten of Example 39.

Example 67

Preparation of Thiacloprid Immunogen

The methodology of Example 64 is used to prepare a clothiadin immunogen using the hapten of Example 57.

Example 68

Immunization Schedule and Harvesting of Antibodies

For the initial immunization, dissolve the immunogen of Example 64 in Freund's Complete Adjuvant. Inoculate female New Zealand white rabbits Inject approximately 25 μg of immunogen at each site. Immunize sheep similarly except that approximately 38 μg of immunogen is injected at each site.

In subsequent immunizations, dissolve the immunogen in Freund's Incomplete Adjuvant.

Rest the animals for four weeks between immunizations and bleed ten days post-immunization.

Administer booster injections and bleed the animals for nine months, at which point they are exsanguinated.

Polyclonal antibodies are harvested using techniques known to those skilled in the art.

Example 69

Preparation of Hapten-Enzyme Conjugates 69.1

The thiamethoxam hapten from Example 1 (3.1 mg), N-hydroxysucinnimide (NHS) (4.0 mg), and EDC (4.6 mg) are combined in a small vial. These materials are dried under a gentle stream of nitrogen for 15 min at room temperature.

69.2

Dry dimethylformamide (2.0 mL) is added and the mixture is sonicated for 1 min. The resulting solution is incubated overnight at room temperature.

69.3

Horseradish peroxidase (8.5 mg) is dissolved in carbonate buffer (2.0 mL, 0.05M pH 9.6), in a small vial. The vial is placed in an ice bath.

69.4

A total of 100 μl of the hapten-NHS-EDC solution from 6.2 is added slowly over 1 hr and the mixture is incubated with stirring for 2 hr.

The reaction mixture is passed over a Sephadex G-25M column equilibrated with PBS (0.01 M, pH 7.2). The enzyme conjugate is collected in the first 3.0 mL of eluate and an equal volume of glycerol is added; store at −20° C.

Example 70

Immunoassay of Canola Seed Treated with Thiamethoxam

A portion of the seed extract is diluted into 1% MeOH/$H_2O$ until the expected concentration of thiamethoxam is brought within range of the calibration curve, 0.5 to 120 parts per billion.

Antibody-coated tubes are labeled and placed in a tube rack such that the first and last tubes are standards and the remaining standards and samples are intermixed. The tube rack grips each tube such that the rack may be inverted without loss of the tubes. An aliquot of a standard or sample (0.5 mL) is added to all corresponding tubes. Enzyme conjugate solution (0.5 mL) is added to all tubes. The rack is shaken gently to mix the contents of all tubes. Tubes are incubated for 20 min at room temperature. The rack is inverted to decant the contents of all tubes. Distilled $H_2O$ is added to all tubes to overflowing using a flip-top wash bottle and the wash is decanted. Tubes are washed an additional three times. After the final wash, the rack is inverted and the tubes are gently tapped upon a clean paper towel to remove excess wash. Enzyme substrate (0.5 mL) is added to all tubes which are incubated for 10 min at room temperature. The rack is shaken gently every 2.5 min during this incubation. Acidic stop solution (1 M HCl, 0.5 mL) is added to all tubes to terminate signal generation. As shown in Table 10, the absorbance of the reaction product is measured at 450 nm. The absorbances of the standards are used to construct a calibration curve, a regression function in the form of Y=m Ln(X)+B. The absorbance of each sample is inserted into the function to determine the concentration of the neonicotinoid pesticide in the diluted sample. The resulting concentration is multiplied by the dilution factor to calculate the amount of neonicotinoid pesticide in the original sample.

TABLE 10

Typical standard curve for the thiamethoxam immunoassay.

| [1]Concentration of Thiamethoxam | Absorbance at 450 nm (Analytical response) |
|---|---|
| 120 | 0.3145 |
| 20 | 0.6636 |
| 3 | 1.0283 |
| 0.5 | 1.3618 |

[1]Units of Parts Per Billion.

The function describing the response of the thiamethoxam standards is generated by regression analysis. This data set produced a standard curve of Y=−0.191 Ln(X)+1.23, r=−0.999 in which Y=the analytical response and X=the concentration of the thiamethoxam standards.

Example 71

Cross Reactivity Test of Crop Seeds Treated with Thiamethoxam 71.1 Extraction of Seeds Samples of treated seed are sub-sampled by randomly adding 50 g of cotton, field corn, sorghum, sweet corn and wheat or 40 g of canola to 8-oz wide-mouth jars. Canola is sub-sampled four times; five sub-samples of the other seed types are used. Solvent (150-ml) is added and the lid is tightly sealed. Cotton is extracted in 5% acetonitrile/water whereas other seeds use a solvent system of 20% methanol/water. The jar is vigorously shaken by hand for 30 seconds and placed in a sonicating water bath at room temperature for 20 minutes. Samples are shaken a second time as previously described. The contents of each jar are allowed to settle for approximately 5 minutes and an aliquot (0.10-ml) is removed for analysis. The aliquot is diluted into 1% methanol/water to bring the residues into the range of the standard curve.

71.2 Immunoassay Analysis

The antibody-coated polystyrene culture tubes are labeled and placed in the tube rack such that the first and last tubes are standards and the remaining standards and samples are mixed. Sample and standard solutions (0.50-ml) are added to the corresponding tubes. A similar volume of enzyme conjugate solution is added. The rack is gently shaken to mix the solutions and set to incubate for 20 min at room temperature. The contents of all tubes are removed by inverting the rack over a stainless steel pan. Each tube is washed to overflowing with distilled water. The rack is inverted over the sink to dump the wash water. Washing is repeated four times. Then the rack is inverted and tapped gently on a paper towel to remove most of the remaining wash. (Some liquid remaining in the tubes does not affect assay results.) Enzyme substrate solution (0.50-ml) is added to the tubes, which are incubated for ten minutes at room temperature. The rack is gently shaken at 2.5 min intervals to ensure the enzyme maintains an ample supply of substrate. Generation of the blue colored signal is terminated by addition of acidic stop solution (0.50-ml). The absorbance of the solution in each tube is measured spectrophotometrically at 450 nm.

The concentration of analyte in the samples is determined from a regression function in the form of y=m ln(x)+b.

71.3 Cross Reactivity Determination

The cross reactivity, or specificity, of the immunoassay is evaluated to determine if other test substances found in seed coatings would interfere with measurement of thiamethoxam. Test substances are dissolved in 1% methanol/water to concentrations ranging from 1000 to 0.01 ng/ml. Aliquots of each concentration are analyzed as described above. The reactivity of each test substance over this range is determined as previously described in Brady, J. F; Turner, J.; Skinner, D. H. "Application of a triasulfuron enzyme immunoassay to the analysis of incurred residues in soil and water samples." J. Agric. Food Chem. 1995, 43:2542–2547.

71.4 Results

Among the test substances analyzed, only thiamethoxam is found to be significantly reactive with the immunoassay (Table 9 below). Therefore, this immunoassay is specific to thiamethoxam.

Sub-samples of treated lots of seed were analyzed by immunoassay and by HPLC. The results of these analyses are shown in Table 11. Table 11 depicts the correlation of mean immunoassay results using a polyclonal antibody and an HPLC analysis of forty seed samples for thiamethoxam. The best fit regression line indicates that similar results were obtained by each method.

TABLE 9

Cross reactivity of the thiamethoxam immunoassay

| Test Substance | [1]Percent Reactivity Relative to Thiamethoxam |
|---|---|
| Thiamethoxam | 100 |
| Clothiadin | <1.0 |
| Imidacloprid | [2]NR |
| Chlorpyrifos | NR |
| Difenoconazole | NR |
| Fludioxonil | NR |
| Pentachloronitrobenzene | NR |
| Metalaxyl | NR |
| Mefenoxam (R-Metalaxyl) | NR |
| Fluxofenim | NR |
| Carboxin | NR |
| Captan | NR |
| Systhane (Myclobutanil) | NR |
| TCMTB | NR |
| Primifos-methyl | NR |
| Thiophanate-methyl | NR |

[1]Reactivity of test substances relative to the reactivity of thiamethoxam expressed as a percentage.
[2]NR, non-reactive.

It will be recognized by persons skilled in the art that numerous variations and modifications may be made to the invention as described above without departing from the spirit or scope of the invention as broadly described.

TABLE 11

Comparison of analytical results obtained by Immunoassay and by HPLC.

| | | Parts Per Million of Thiamethoxam Found by | | | | | | |
|---|---|---|---|---|---|---|---|---|
| Seed type | Sample | Immunoassay [1]Replicate Analyses | | | | | [1]Mean | HPLC |
| Canola | 294642 | 3517 | 2586 | 3403 | 4139 | 4327 | 3594 | 3724 |
| | 294681 | 4191 | 3416 | 3643 | 3591 | 4718 | 3912 | 3915 |
| | 294682 | 3034 | 3299 | 2687 | 3534 | 4254 | 3362 | 3769 |

TABLE 11-continued

Comparison of analytical results obtained by Immunoassay and by HPLC.

| | | Parts Per Million of Thiamethoxam Found by | | | | | | |
|---|---|---|---|---|---|---|---|---|
| Seed type | Sample | Immunoassay [1]Replicate Analyses | | | | | [1]Mean | HPLC |
| | 294683 | 3264 | 3104 | 3614 | 3860 | 3445 | 3457 | 3875 |
| | 294684 | 2761 | 3367 | 3617 | 3685 | 3409 | 3368 | 3920 |
| Sorghum | 294643 | 1659 | 1865 | 1662 | 1661 | 1929 | 1755 | 1732 |
| | 294643 | 1613 | 1654 | 1678 | 1771 | 1998 | 1743 | 1732 |
| | 294685 | 1348 | 1855 | 1601 | 1984 | 1979 | 1753 | 1853 |
| | 294686 | 1717 | 2054 | 1966 | 1981 | 1980 | 1940 | 1870 |
| | 294687 | 1943 | 1880 | 2244 | 1767 | 2165 | 2000 | 1861 |
| | 294688 | 1972 | 1821 | 1746 | 1864 | 1626 | 1806 | 1923 |
| Wheat | 294644 | 651 | 664 | 611 | 573 | 612 | 622 | 624 |
| | 294689 | 628 | 688 | 684 | 569 | 741 | 662 | 712 |
| | 294689 | 690 | 732 | 655 | 753 | 710 | 708 | 712 |
| | 294690 | 930 | 817 | 690 | 794 | 898 | 826 | 745 |
| | 294691 | 757 | 565 | 625 | 700 | 806 | 691 | 731 |
| | 294692 | 1057 | 994 | 893 | 740 | 845 | 906 | 731 |
| | 294692 | 915 | 861 | 604 | 658 | 599 | 727 | 731 |
| Cotton | 294645 | 2149 | 2091 | 2309 | 2320 | 2505 | 2275 | 2694 |
| | 294677 | 2774 | 2477 | 2602 | 3369 | 3329 | 2910 | 2829 |
| | 294678 | 2220 | 3587 | 2945 | 2870 | 2853 | 2895 | 2907 |
| | 294679 | 2427 | 3275 | 2471 | 2795 | 2538 | 2701 | 2757 |
| | 294680 | 1967 | 2006 | 2255 | 2056 | 2119 | 2080 | 2933 |
| | 294680 | 2963 | 2750 | 2510 | 2934 | 2481 | 2728 | 2933 |
| | 294645 | 2115 | 2576 | 2865 | 3146 | 2649 | 2670 | 2694 |
| Sweet corn | 298296 | 469 | 428 | 364 | 375 | 455 | 418 | 390 |
| | 298297 | 750 | 390 | 480 | 514 | 499 | 527 | 397 |
| | 298298 | 554 | — | 476 | 426 | 481 | 484 | 368 |
| | 298299 | 456 | 440 | 377 | 412 | 387 | 414 | 372 |
| | 298300 | 448 | 343 | 375 | 388 | 410 | 393 | 385 |
| | 298301 | 3931 | 3625 | 4350 | 4083 | 4485 | 4095 | 3640 |
| | 298302 | 4854 | 5058 | 4558 | 4286 | 5237 | 4798 | 4189 |
| | 298303 | 3431 | 3587 | 3176 | 3835 | 4296 | 3665 | 3657 |
| | 298304 | 5379 | 5428 | 4246 | 4084 | 3697 | 4567 | 3792 |
| | 298305 | 3107 | 4301 | 2881 | 4397 | 4692 | 3876 | 3859 |
| Field corn | 298307 | 469 | 464 | 567 | 451 | 422 | 475 | 424 |
| | 298308 | 409 | 384 | 409 | 422 | 386 | 402 | 389 |
| | 298309 | 379 | 408 | 368 | 378 | 333 | 373 | 400 |
| | 298310 | 428 | 395 | 493 | 417 | 552 | 367 | 373 |
| | 298311 | 320 | 407 | 307 | 402 | 398 | 457 | 383 |
| | 298312 | 3050 | 3656 | 2645 | 3622 | 3827 | 3360 | 3038 |
| | 298313 | 4322 | 3694 | 2955 | 3397 | 3185 | 3511 | 3529 |
| | 298314 | 3602 | 3347 | 3804 | 3055 | 3972 | 3556 | 3681 |
| | 298315 | 3563 | 3301 | 3271 | 3445 | 4037 | 3523 | 3712 |
| | 298316 | 4326 | 4903 | 5118 | 4590 | 4873 | 4762 | 3661 |

[1]Replicate analyses (five) of each sample were conducted by immunoassay. The mean value of all immunoassay analyses for each sample was compared to the HPLC result for that sample by regression analysis. This produced a regression function of $Y = 1.00 X + 10.9$, $r = .976$, $N = 40$ where Y = PPM Thiamethoxam found by Immunoassay and X = PPM Thiamethoxam found by HPLC.

What is claimed is:

1. A protein conjugate of the formula (II)

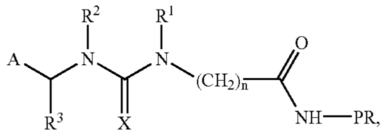

wherein A is 2-chloropyrid-5-yl or 2-chlorothiazol-5-yl;

$R^3$ is hydrogen or $C_1$–$C_4$alkyl;

$R^1$ and $R^2$ independently are hydrogen or $C_1$–$C_4$alkyl or $R^1$ and $R^2$ are taken together with the nitrogen atoms to which they are attached to form an imidazoline or an oxadiazine ring;

n is an integer of from 1 to 4;

X is N—$NO_2$ or N—CN; and

PR an immunogenic is a protein residue.

2. An antibody useful in an immunoassay of a sample to determine the amount of a neonicotinoid insecticide, wherein said antibody (I) is a polyclonal antibody produced by immunizing an animal with a neonicotinoid hapten conjugated to an immunogenic carrier protein and (II) specifically binds to the neonicotinoid insecticide and wherein the antibody is selective for a compound of the formula (I)

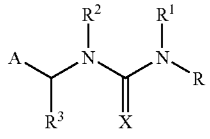

wherein A is 2-chloroDyrid-5-yl or 2-chlorothiazol-5-yl;

R and $R^3$ independently are hydrogen or $C_1$–$C_4$alkyl;

$R^1$ are $R^2$ independently are hydrogen or $C_1$–$C_4$alkyl or $R^1$ and $R^2$ are taken together with the nitrogen atoms to which they are attached to form an imidazoline or an oxadiazine ring; and X is N—$NO_2$ or N—CN; wherein the antibody is prepared using the immunogen of claim 1.

3. The antibody according to claim 2, wherein said antibody is selective for a compound selected from the group consisting of imidacloprid, nitenpyram, acetamiprid, thiamethoxam, thiacloprid and clothiadin.

4. A compound of the formula (IA)

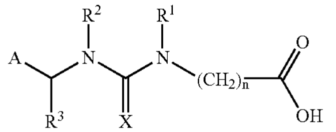

wherein A is 2-chloropyrid-5-yl or 2-ch lorothiazol-5-yl;

$R^3$ is hydrogen or $C_1$–$C_4$alkyl;

$R^1$ and $R^2$ independently are hydrogen or $C_1$–$C_4$alkyl or $R^1$ and $R^2$ are taken together with the nitrogen atoms to which they are attached to form an imidazoline or an oxadiazine ring;

n is an integer from 1 to 4; and

X is N—$NO_2$ or N—CN.

5. A compound according to claim 4 of the formula

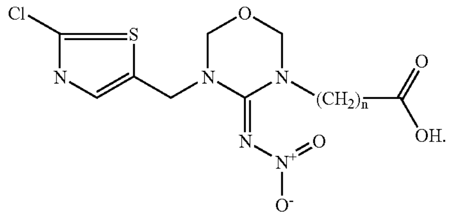

6. A compound according to claim 5 of the formula

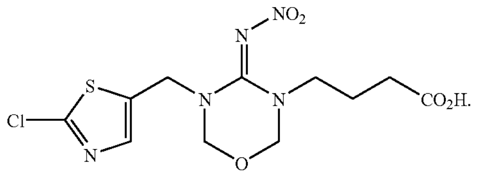

7. A compound according to claim 4 of the formula

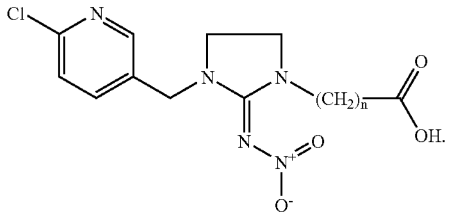

8. A compound according to claim 7 of the formula

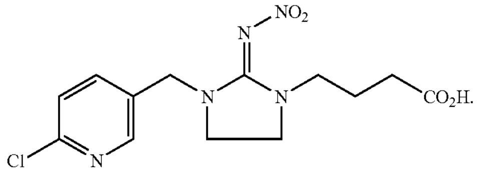

9. A protein conjugate according to claim 1 of the formula

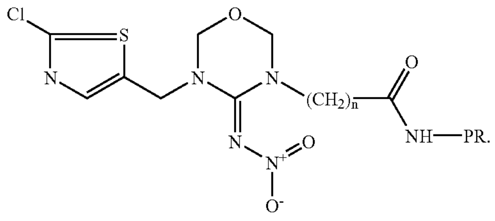

10. A protein conjugate according to claim 1 of the formula

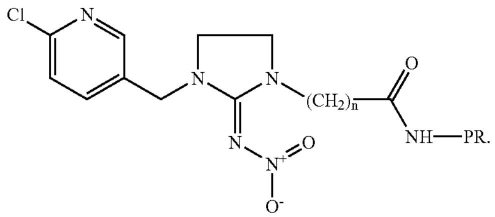

11. A method of determining the concentration of a neonicotinoid insecticide in a sample, comprising the steps of:

(a) providing a solid phase with an immobilized antibody selective for said neonicotinoid insecticide wherein the said neonicotinoid insecticide is a compound of the formula (I)

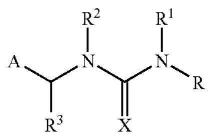

wherein A is 2-chloropyrid-5-yl or 2-chlorothiazol-5-yl;

R and $R^3$ independently are hydrogen or $C_1$–$C_4$alkyl;

$R^1$ are $R^2$ independently are hydrogen or $C_1$–$C_4$alkyl or $R^1$ and $R^2$ are taken together with the nitrogen atoms to which they are attached to form an imidazoline or an oxadiazine ring; and X is N—$NO_2$ or N—CN, wherein the antibody is prepared using the immunogen of claim 1;

(b) contacting said sample with the immobilized antibody in the presence of a known amount of a neonicotinoid insecticide hapten-enzyme conjugate;

(c) washing the solid phase of step (b) to remove any unbound hapten-enzyme conjugate or sample;

(d) reacting a chromogenic substrate specific for said hapten-enzyme conjugate with the washed solid phase of step (c) in order to generate a chromogen; and (e) measuring the amount of the chromogen produced by step (d) in order to determine the amount of antibody-bound hapten-enzyme conjugate and hence the amount of neonicotinoid insecticide in said sample.

12. A method according to claim 11 wherein said sample is obtained by extracting a plant propagation material in a suitable solvent.

13. A method according to claim 12 wherein said plant propigation material is a seed.

14. A method according to claim 13 wherein said seed is selected from the group consisting of canola, sorghum, wheat, cotton, field corn or sweet corn.

15. A method according to claim 11 wherein said antibody is a polyclonal antibody produced by immunizing an animal with a neonicotinoid insecticide conjugated to an immunogenic carrier protein.

16. A method according to claim 15 wherein said immunogenic carrier protein is a carrier molecule selected from the group consisting of a purified protein derivative (PPD, Tuberculin) from Diptheria virus, bovine serum albumin, cationized bovine serum albumin, human serum albumin, ovalbumin and keyhole limpet hemocyanin.

17. A kit useful for an immunoassay of a sample to determine the amount of a neonicotinoid insecticide, wherein the kit comprises in combination in one or more containers:

(a) a solid phase with an immobilized antibody selective for said neonicotinoid insecticide wherein the said neonicotinoid insecticide is a compound of the formula (I)

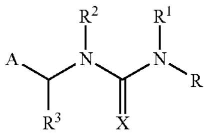

wherein A is 2-chloropyrid-5-yl or 2-chlorothiazol-5-yl;

R and $R^2$ independently are hydrogen or $C_1$–$C_4$alkyl;

$R^1$ are $R^2$ independently are hydrogen or $C_1$–$C_4$alkyl or $R^1$ and $R^2$ are taken together with the nitrogen atoms to which they are attached to form an imidazoline or an oxadiazine ring; and X is N—$NO_2$ or N—CN; wherein the antibody is prepared using the immunogen of claim 1;

(b) an enzyme conjugate comprising an enzyme conjugated to a neonicotinoid hapten.

18. The kit of claim 17 wherein the antibody is a polyclonal antibody produced by immunizing an animal with a neonicotinoid conjugated to an immunogenic carrier protein.

19. The kit of claim 18 wherein the enzyme is horseradish peroxidase.

20. The kit of claim 17 wherein the antibody specifically binds to a neonicotinoid insecticide selected from the group consisting of imidacloprid, nitenpyram, acetamiprid, thiamethoxam, thiacloprid and clothiadin.

21. The protein conjugate according to claim 1, wherein the immunogenic protein residue is a carrier molecule selected from the group consisting of a purified protein derivative (PPD, Tuberculin) from Diptheria virus, bovine serum albumin, cationized bovine serum albumin, human serum albumin, ovalbumin and keyhole limpet hemocyanin.

22. The protein conjugate according to claim 1, wherein the immunogenic protein residue is an enzyme residue selected from the group consisting of alkaline phosphatase, horseradish peroxidase and beta-galactosidase.

* * * * *